United States Patent [19]

Fuchs et al.

[11] Patent Number: 5,637,700

[45] Date of Patent: *Jun. 10, 1997

[54] PURIFICATION OF CAPROLACTAM

[75] Inventors: Hugo Fuchs, Ludwigshafen; Gerald Neubauer, Weinheim; Claus-Ulrich Priester, Ludwigshafen, all of Germany

[73] Assignee: BASF Aktiengesellschaft, Ludwigshafen, Germany

[*] Notice: The term of this patent shall not extend beyond the expiration date of Pat. No. 5,350,847.

[21] Appl. No.: 297,719

[22] Filed: Aug. 30, 1994

Related U.S. Application Data

[63] Continuation of Ser. No. 113,081, Aug. 30, 1993, Pat. No. 5,350,847.

[30] Foreign Application Priority Data

Sep. 8, 1992 [DE] Germany .................. 42 29 915.2

[51] Int. Cl.$^6$ .................................................. C07D 201/12

[52] U.S. Cl. .................................................. 540/540
[58] Field of Search .................................... 540/540

[56] References Cited

U.S. PATENT DOCUMENTS

| 4,178,287 | 12/1979 | Mattone et al. .............. 260/239.3 |
| 5,350,847 | 9/1994 | Fuchs et al. .............. 540/540 |

FOREIGN PATENT DOCUMENTS

| 892926 | 5/1944 | France .................. 540/540 |
| 1148390 | 12/1957 | France .................. 540/540 |
| 2347351 | 12/1977 | France .................. 540/540 |
| 858702 | 12/1952 | Germany .................. 540/540 |

*Primary Examiner*—Robert T. Bond
*Attorney, Agent, or Firm*—Keil & Weinkauf

[57] ABSTRACT

Caprolactam is purified by oxidative treatment in which mixtures which essentially contain the caprolactam to be purified and unsaturated lactams are treated with oxygen or an oxygen-containing gas mixture in an alkaline medium.

6 Claims, No Drawings

PURIFICATION OF CAPROLACTAM

This application is a continuation of application Ser. No. 08/113,081 filed 30 Aug. 1993, now U.S. Pat. No. 5,350,847.

The present invention relates to a process for purifying caprolactam by oxidative treatment.

Caprolactam is the starting material for the preparation of polycaprolactam (nylon 6) and is usually purified in industrial processes, after it has been produced by Beckmann rearrangement of the appropriate oxime, by extraction and distillation. Further purification is possible by additional measures such as reextraction and/or treatment with ion exchangers (see Ullmann's Encyclopedia of Industrial Chemistry Vol. A 5 Caprolactam, pp 31–50 (1986)).

Depending on the process for the preparation of caprolactam and the quality of the starting materials such as cyclohexanone, the rearrangement of the oxime to the lactam may result in impurities which impair the quality of the caprolactam. Its quality is usually characterized by the permanganate absorption number, for example. Impurities generally result in an increase in the permanganate absorption number (PAN).

Unwanted impurities which have a particularly large effect on the PAN are generally unsaturated lactams. They are usually formed from unsaturated ketones and cannot be removed satisfactorily by extraction and distillation. There has thus been no lack of attempts to improve the quality of caprolactam by reductive or oxidative treatment.

Thus, CH-B 326 951 describes the oxidative treatment of caprolactam-containing mixtures with potassium permanganate. DE-B 950 726 describes oxidative treatment with potassium permanganate, hydrogen peroxide or persulfuric acid to improve the quality of caprolactam obtained from nylon 6.

The oxidative treatment with potassium permanganate which is generally employed has the particular disadvantage that manganese dioxide is produced in the reaction and must be removed by filtration and subsequently disposed of.

It is an object of the present invention to provide a process for purifying caprolactam by oxidative treatment which does not have the abovementioned disadvantages.

We have found that this object is achieved by a process for purifying caprolactam by oxidative treatment, wherein mixtures containing the caprolactam to be purified and unsaturated lactams are treated with oxygen or an oxygen-containing gas mixture in an alkaline medium.

Since the reaction of caprolactam with air or oxygen usually results in unwanted products, the success of the process according to the invention was unexpected (see Kunststoffe, 57 (1967) 49–52).

In the process according to the invention, oxygen or an oxygen-containing gas mixture is introduced into mixtures which essentially contain caprolactam, unsaturated lactams and preferably at least one oxide or hydroxide of an alkali metal or alkaline earth metal.

The caprolactam-containing mixtures according to the invention usually contain from 95 to 99.9, preferably from 98 to 99.9, % by weight of caprolactam and from 0.0005 to 0.1, preferably from 0.001 to 0.02, % by weight of unsaturated lactams. They may also contain other compounds such as substituted lactams and aliphatic amides in amounts in the range from 0.001 to 5% of the weight of caprolactam.

Used in a particular embodiment are caprolactam-containing mixtures which are derived from industrial processes and which contain the unsaturated lactams in increased amounts, for example from distillation foreruns or distillates from workup of the bottom product.

Unsaturated lactams which may be mentioned are, for example, 3,4- and 4,5-dehydrocaprolactam.

An alkaline media is preferably obtained by adding an oxide or hydroxide or an alkali metal or alkaline earth metal to the mixtures to be purified. Examples which may be mentioned are lithium, sodium, potassium, magnesium, calcium, strontium and barium hydroxides, preferably sodium and potassium hydroxides, particularly preferably sodium hydroxide, and magnesium, calcium, strontium and barium oxides, preferably magnesium and calcium oxides.

The oxides and hydroxides of the alkali metals and alkaline earth metals can be added in solution or in solid form, preferably in solid form. The amount of these basic compounds can vary within wide limits. The amounts employed are generally in the range from 0.001 to 2, preferably from 0.05 to 1.0, particularly preferably from 0.1 to 0.2, % of the weight of caprolactam.

Observations to date indicate that the amount of oxygen or of an oxygen-containing gas mixture, preferably air, is not critical. Air is preferably employed in an amount in the range from 0.1 to 100, preferably from 5 to 50, l/kg of caprolactam. The gas can be introduced, for example, through nozzles in co- or countercurrent in a column or by, for example, forcing the gas or gas mixture directly through the liquid in a tank by means of nozzles.

The oxidative treatment is generally carried out at a temperature at which the mixture is liquid. This is usually the case in the range from 70° to 150° C., preferably from 80° to 100° C. If the caprolactam-containing mixture contains water it is also possible to carry out the reaction below 70° C. as long as the mixture is liquid. Unwanted byproducts are generally to be expected above 150° C.

The water content of the caprolactam-containing mixtures is preferably not more than 1, particularly preferably not more than 0.01, % of the weight of the caprolactam.

Observations to date likewise indicate that the reaction pressure is not critical and can be in the range from 10 to 500 kPa, atmospheric pressure being expedient.

The duration of the oxidative treatment usually depends essentially on the reaction temperature and is generally in the range from 1 to 120, preferably from 10 to 60 min.

The oxidative treatment is normally followed by further purification of the caprolactamin a conventional manner, for example by distillation.

The process according to the invention has the advantage over other oxidative processes, especially with potassium permanganate, that unwanted unsaturated lactams are eliminated without disposal problems arising, for example due to manganese dioxide. The permanganate absorption number can be distinctly improved by the process according to the invention.

EXAMPLES

Example 200 g of a mixture taken from the high-boiling fraction from the distillation of caprolactam obtained from cyclohexanone by oximation and containing 0.07% by weight of impurities such as amides and substituted lactams, plus 0.0028% by weight of unsaturated lactams, were mixed with 0.2 g of NaOH at 80° C. 10 l of air were passed per hour through the melt. After 1 h, the caprolactam treated with air in this way was analyzed by gas chromatography. The result is to be found in the Table below.

Comparative Example The process was analogous to that in the above Example, except that no NaOH was added. The result is to be found in the Table below.

TABLE

|  | Untreated | Ex. | Comp. |
|---|---|---|---|
| Total impurities [ppm] | 700 | 550 | 590 |
| 3,4- + 4,5-dehydro-caprolactam [ppm] | 28 | 2 | 28 |
| Permanganate absorption number PAN | 48 | 33 | 42 |
| Volatile bases [meq/kg] | 0.83 | 0.90 | 1.0 |

For the photometric determination of the permanganate absorption number, in each case 1.000 g of the mixture to be investigated was placed in a 100 ml volumetric flask.

Subsequently distilled, oxygen-free water of pH 6.2–6.5 was added up to the mark, mixing thoroughly. A second 100 ml volumetric flask was filled to the mark only with distilled oxygen-free water of pH 6.2–6.5. Both flasks were equilibrated in a thermostat at 25° C. (about 30 min) and then 2.00 ml of a 0.01N potassium permanganate solution were added first to the water and immediately thereafter to the caprolactam-containing solution. A stopclock was started at the beginning of the addition of potassium permanganate. Both volumetric flasks were immediately stoppered, mixed thoroughly and returned to the thermostat. After about 9 min. both solutions were introduced into two 5 cm cuvettes which were then placed in a spectrophotometer. 10 minutes±10 sec after the addition of the potassium permanganate solution, the extinction of the caprolactam solution at 420 nm was measured with the permanganate-treated water as reference. The permanganate absorption number is then obtained by multiplying the difference between the extinctions of the two solutions by the factor 100.

The content of volatile bases was determined by the KJeldahl method in a Parnas apparatus. For each measurement, 100 ml of 4 mol/l sodium hydroxide solution were introduced into the KJeldahl flask in the apparatus, and 20±0.1 g of the solution to be investigated were added with a total of 70 ml of distilled water. Then steam was blown through the solution in the Kjeldahl flask for about 5 min until 50 ml of the flask contents had distilled into a receiver which contained 5.00 ml of 0.02 mol/l hydrochloric acid, 30 ml of distilled water and 5 drops of an indicator solution (prepared from 0.3 g of methyl red and 0.3 g of methylene blue in 400 ml of methanol). The excess hydrochloric acid in the receiver was back-titrated against 0.02 mol/l sodium hydroxide solution (A ml used). Determination on a blank without addition of a caprolactam solution gave the content of volatile bases in the sodium hydroxide solution used (B ml used). The content of volatile bases can then be calculated from $(B-A)\times 0.02\times 1000/20 = B-A$ meq/kg.

We claim:

1. A process for purifying caprolactam by oxidative treatment which comprises: adding an oxide or hydroxide of an alkali metal or alkaline earth metal to a liquid mixture containing the caprolactam to be purified and unsaturated lactams to provide an alkaline medium, and thereafter passing oxygen or an oxygen-containing gas mixture through the liquid mixture, whereby the reaction time is in the range of from 1 to 120 minutes and the reaction temperature is less than 150° C.

2. A process as defined in claim 1, wherein the alkaline medium is provided by adding sodium hydroxide, calcium oxide or magnesium oxide to the liquid mixture.

3. A process as defined in claim 1, wherein from 0.05 to 1.0 percent by weight of the oxide or hydroxide is added to the liquid mixture based on the weight of caprolactam that is present.

4. A process as defined in claim 1, wherein the oxidative treatment is carried out at a temperature of from 80° to 100° C.

5. A process as defined in claim 1, wherein the liquid mixture contains not more than 1% by weight of water.

6. A process to reduce the content of 3,4- and 4,5-dehydrocaprolactam in a mixture comprising caprolactam and 3,4- and 4,5-dehydrocaprolactam which comprises: adding an oxide or hydroxide of an alkali metal or alkaline earth metal to a liquid mixture containing the caprolactam to be purified and unsaturated lactams to provide an alkaline medium, and thereafter passing oxygen or an oxygen-containing gas mixture through the liquid mixture, whereby the reaction time is in the range of from 1 to 120 minutes and the reaction temperature is less than 150° C.

* * * * *

UNITED STATES PATENT AND TRADEMARK OFFICE
CERTIFICATE OF CORRECTION

PATENT NO.: 5,637,700

DATED: June 10, 1997

INVENTOR(S): FUCHS et al.

It is certified that error appears in the above-identified patent and that said Letters Patent is hereby corrected as shown below:

Column 4, claim 6, line 35, "dehydrocaprolactamin" should read --dehydrocaprolactam in--.

Signed and Sealed this

Twelfth Day of August, 1997

Attest:

BRUCE LEHMAN

Attesting Officer

Commissioner of Patents and Trademarks